(12) United States Patent
Xu

(10) Patent No.: US 9,811,642 B2
(45) Date of Patent: Nov. 7, 2017

(54) METHODS FOR SHAPE COMPARISON BETWEEN DRUG MOLECULES

(71) Applicant: Sun Yat-Sen University, Guangzhou (CN)

(72) Inventor: Jun Xu, Guangzhou (CN)

(73) Assignee: IPRECISION MEDICINE TECHNOLOGY, INC., Guangzhou (CN)

( * ) Notice: Subject to any disclaimer, the term of this patent is extended or adjusted under 35 U.S.C. 154(b) by 721 days.

(21) Appl. No.: 14/351,978

(22) PCT Filed: Nov. 16, 2012

(86) PCT No.: PCT/CN2012/084713
§ 371 (c)(1),
(2) Date: Apr. 15, 2014

(87) PCT Pub. No.: WO2014/012309
PCT Pub. Date: Jan. 23, 2014

(65) Prior Publication Data
US 2014/0278284 A1 Sep. 18, 2014

(30) Foreign Application Priority Data
Jul. 16, 2012 (CN) .......................... 2012 1 0245107

(51) Int. Cl.
*G06F 17/50* (2006.01)
*G06F 7/60* (2006.01)
(Continued)

(52) U.S. Cl.
CPC .......... *G06F 19/706* (2013.01); *G06F 19/704* (2013.01); *G06F 19/16* (2013.01); *G06F 19/705* (2013.01)

(58) Field of Classification Search
CPC .... G06F 19/706; G06F 19/704; G06F 19/705; G06F 19/16
(Continued)

(56) References Cited

U.S. PATENT DOCUMENTS

2003/0167159 A1 9/2003 Goddard et al.

FOREIGN PATENT DOCUMENTS

WO 03019140 A2 3/2003

OTHER PUBLICATIONS

Guo, Ming et al., "Study on the calculation method for molecular volume of chemical compounds", Journal of zhejiang university, Sep. 2003, vol. 30, No. 5, pp. 554-560 (English Abstract provided).
(Continued)

*Primary Examiner* — Saif Alhija
(74) *Attorney, Agent, or Firm* — Muncy, Geissler, Olds & Lowe, P.C.

(57) ABSTRACT

The invention relates to a calculating method for molecular volume and shape comparison of two molecules. The method includes steps of loading in three-dimensional structure information of a first molecule, the three-dimensional structure information comprising type and coordinate values of each atom contained in the first molecule; obtaining respective van der Waals radius based on the type of respective atom contained in the first molecule, converting the three-dimensional structure information into a group of Gaussian spheres representing atoms in the first molecule; calculating overlap volume for each pair of Gaussian spheres; calculating the weight of each Gaussian sphere; calculating self-overlap volume of the first molecule, the self-overlap volume being used as a volume of the first molecule. The present invention is useful mathematical expression of molecular shape, shape comparison of drug molecules, and pharmacophore comparison of drug mol-
(Continued)

ecules, which comparisons, in turn, useful for virtual screening of drug molecules.

3 Claims, 6 Drawing Sheets

(51) Int. Cl.
*G06F 17/10* (2006.01)
*G06F 19/00* (2011.01)
*G06F 19/16* (2011.01)

(58) Field of Classification Search
USPC .......................................................... 703/1, 2
See application file for complete search history.

(56) References Cited

OTHER PUBLICATIONS

International Search Repor for Application No. PCT/CN2012/084713 dated Apr. 18, 2013.
Shang, Zhicai et al., "Monte carlo simulation calculation of volume and surface area of molecule", Acta physico-chimica sinica,. Dec. 1997, vol. 13, No. 12, pp. 1097-1100 (English Abstract provided.).

METHODS FOR SHAPE COMPARISON BETWEEN DRUG MOLECULES

CROSS-REFERENCE TO RELATED APPLICATIONS

The present application is a national phase entry under 35 U.S.C. §371 of International Application No. PCT/CN2012/084713 filed Nov. 16, 2012, which claims priority from Chinese Patent Application No. 201210245107.3, filed Jul. 16, 2012, all of which are incorporated herein by reference.

FIELD OF THE INVENTION

The present invention relates to design and screening of drug molecules, in particular, to a method for shape comparison between drug molecules.

BACKGROUND OF THE INVENTION

Shape matching and quantitative comparison of three-dimensional shapes and pharmacophores (a group of atoms in a molecule, having particular properties) between two molecules are main methods in the field of drug design. The volume of a molecule is relevant to its shape which, in turn, determines the physical and chemical properties of the molecule and thus the bioactivity thereof.

Conventionally, a shape of a molecule was calculated by a set of fused hard spheres, where each hard sphere represents an atom with its van der Waals radius. In a hard sphere model, the volume density function F(r) takes a simple value, either 1 if the coordinate r is within the molecule or 0 if r is outside. Therefore, the volume density function can be expressed in terms of the volume density functions of individual atoms as Formula (1):

$$F(r) = \sum_i f_i(r) - \sum_{i<j} f_i(r)f_j(r) + \sum_{i<j<k} f_i(r)f_j(r)f_k(r) - \sum_{i<j<k<l} f_i(r)f_j(r)f_k(r)f_l(r) + \ldots \quad (1)$$

$$= 1 - \prod_i [1 - f_i(r)]$$

wherein $f_i(r)$ represents the volume density of atom i.

As shown in FIG. 1, for a diatomic molecule, the volume is calculated by subtracting overlap of the two atoms from the summation volume, i.e, V=VA+VB−VAB. For a tri-atomic molecule, the volume is calculated by alternative "inclusion" and "exclusion" terms: V=VA+VB+VC−VAB−VAC−VBC+VABC. For any molecules, the volume is also calculated by alternative "inclusion" and "exclusion" terms, taking advantage of Formula (2):

$$V = \int F(r)dr \quad (2)$$

$$= \sum_i v_i - \sum_{i<j} v_{ij} + \sum_{i<j<k} v_{ijk} - \sum_{i<j<k<l} v_{ijkl} + \ldots$$

wherein $v_i$ represents the volume of atom i, $v_{ij}$ represents the (second order) overlap of atoms i and j, $v_{ijk}$ represents the (third order) overlap of atoms i, j and k, and so on. For a molecule having N atoms, the summation generally goes on up to the order of N−1.

One of the main disadvantages of the molecular shape calculation method is prolonged calculation time and decreased accuracy due to the discontinuity of the derivative of the volume obtained through the hard sphere model with respect to the atom coordinate.

SUMMARY OF THE INVENTION

In order to overcome the disadvantages identified in the prior method, the present invention provides a method for shape comparison of drug molecules, comprising steps of:

(11) loading in three-dimensional structure information of a first molecule, the three-dimensional structure information comprising type and coordinate values of each atom contained in the first molecule;

(12) obtaining respective van der Waals radius based on the type of respective atom contained in the first molecule, converting the three-dimensional structure information into a group of Gaussian spheres representing atoms in the first molecule, each of the set of Gaussian spheres having a radius equal to the van der Waals radius of respective atom and a position equal to the coordinate position of respective atom;

(13) calculating overlap volume for each pair of Gaussian spheres, wherein the $ij^{th}$ pair of Gaussian spheres consists of the $i^{th}$ and the $j^{th}$ Gaussian spheres and has a overlap volume $v_{ij}$;

(14) calculating the weight of each Gaussian sphere, the weight of the $i^{th}$ Gaussian sphere $$w_i = \frac{v_i}{v_i + k\sum_{j\neq i} V_{ij}},$$

wherein $v_i$ is the volume of the $i^{th}$ Gaussian sphere, and k is a constant;

(15) calculating self-overlap volume of the first molecule $$V = \sum_{i\in A, j\in A} w_i w_j v_{ij},$$

the self-overlap volume being used as a volume of the first molecule, wherein $w_i$ is the weight of the $i^{th}$ Gaussian sphere, $w_j$ is the weight of the $j^{th}$ Gaussian sphere, $v_{ij}$ is the overlap volume of the $i^{th}$ and the $j^{th}$ Gaussian spheres, and A is a set of all Gaussian sphere in the first molecule.

Furthermore, the constant k has a value between 0.5 and 1.0.

The present invention also provide a method for shape comparison between drug molecules, comprising steps of:

(31) loading in three-dimensional structure information for a first molecule and a second molecule and calculating self-overlap volumes of the first and second molecules, the calculation comprising steps of:

loading in three-dimensional structure information of the first molecule, the three-dimensional structure information comprising type and coordinate values of each atom contained in the first molecule;

obtaining respective van der Waals radius based on the type of respective atom contained in the first molecule, converting the three-dimensional structure information into a group of Gaussian spheres representing atoms in the first molecule, each of the set of Gaussian spheres having a radius equal to the van der Waals radius of respective atom and a position equal to the coordinate position of respective atom;

calculating overlap volume for each pair of Gaussian spheres in the first molecule, wherein the $ij^{th}$ pair of Gaussian spheres in the first molecule consists of the $i^{th}$ and the $j^{th}$ Gaussian spheres and has an overlap volume $v_i$;

calculating the weight of each Gaussian sphere in the first molecule, the weight of the $i^{th}$ Gaussian sphere in the first molecule $$w_i = \frac{v_i}{v_i + k \sum_{j \neq 1} V_{ij}},$$

wherein $v_i$ is the volume of the $i^{th}$ Gaussian sphere, and k is a constant;

calculating self-overlap volume of the first molecule $$V_1 = \sum_{i \in A, j \in A} w_i w_j v_{ij},$$

wherein A is a set of all Gaussian sphere in the first molecule;

loading in three-dimensional structure information of the second molecule, the three-dimensional structure information comprising type and coordinate values of each atom contained in the second molecule;

obtaining respective van der Waals radius based on the type of respective atom contained in the second molecule, converting the three-dimensional structure information into a group of Gaussian spheres representing atoms in the second molecule, each of the set of Gaussian spheres having a radius equal to the van der Waals radius of respective atom and a position equal to the coordinate position of respective atom;

calculating overlap volume for each pair of Gaussian spheres in the second molecule, wherein the $ij^{th}$ pair of Gaussian spheres in the second molecule consists of the $i^{th}$ and the $j^{th}$ Gaussian spheres and has an overlap volume $v_{ij}'$;

calculating the weight of each Gaussian sphere in the second molecule, the weight of the $i^{th}$ Gaussian sphere in the second molecule $$w_i' = \frac{v_i'}{v_i' + k' \sum_{j \neq 1} v_{ij}'},$$

wherein $v_i'$ is the volume of the $i^{th}$ Gaussian sphere, and k' is a constant;

calculating self-overlap volume of the second molecule $$V_2 = \sum_{i \in B, j \in B} w_i' w_j' v_{ij}',$$

wherein B is a set of all Gaussian sphere in the second molecule;

(32) calculating intermolecular volumes of the first and second molecules in various overlap situations, selecting the maximum volume between molecules;

(33) determining the similarity between the first and second molecules based on the volume of the first molecule, the volume of the second molecule and the maximum volume between the two molecules, the similarity being the result of the shape comparison between the two molecules.

Furthermore, the intermolecular volume of step (32) is an overlap volume between molecules, which is calculated by a step of:

calculating the overlap volume $$V_{12} = \sum_{i \in A, j \in B} w_i w_j' v_{ij}''$$

of the first and second molecules in various overlap situations, wherein $v_{ij}''$ is an overlap volume of the $i^{th}$ atom in the first molecule and the $j^{th}$ atom in the second molecule, the maximum value $V_{12}^{Max}$ serves as the maximum overlap volume between molecules.

In step (33), the similarity $$S_{12} = \frac{V_{12}^{Max}}{V_1 + V_2 - V_{12}^{Max}}$$

between the first and second molecules is calculated and serves as the result of the shape comparison.

Furthermore, the intermolecular volume of step (32) is a composite overlap volume between molecules, which is calculated by steps of:

(51) finding out pharmacophores and their positions in each of the molecules;

(52) determining types of each of the pharmacophores in each of the molecules;

(53) calculating a self composite overlap volume $$O_1 = V_1 + \sum_{i \in A, j \in A} F_{ij}$$

of the first molecule, wherein $F_{ij}$ is the overlap volume between the $i^{th}$ pharmacophore and the $j^{th}$ pharmacophore, and the summation over $F_{ij}$ is limited only to pharmacophores of same type;

(54) calculating a self composite overlap volume $$O_2 = V_2 + \sum_{i \in B, j \in B} F_{ij}'$$

of the first molecule, wherein is the overlap volume between the $i^{th}$ pharmacophore and the $F^{ij}$' pharmacophore, and the summation over $F_{ij}'$ is limited only to pharmacophores of same type;

(55) calculating a composite overlap volume between the first and the second molecules $$O_{12} = V_{12} + \sum_{i \in A, j \in B} F_{ij}'',$$

wherein $F_{ij}'$ is the overlap volume between the $i^{th}$ pharmacophore in the first molecule and the $j^{th}$ pharmacophore in the second molecule, and the summation over $F_{ij}'$ is limited only to pharmacophores of same type;

(56) calculating composite overlap volumes $O_{12}$ between the first and the second molecules under various overlap situations and selecting the maximum value $O_{12}^{Max}$ as the maximum volume between molecules;

wherein step (33) specifically includes a step of calculating the similarity $$S_{12} = \frac{O_{12}^{Max}}{O_1 + O_2 - O_{12}}$$

between the first and second molecules and outputting the similarity $S_{12}$ as the result for the shape comparison for the two molecules.

Furthermore, the k is ranged between 0.5 and 1.0, and k' is ranged between 0.5 and 1.0.

The present method reduces the complexity of calculation for quantitative comparison of three-dimensional shapes of molecules, while increasing calculation accuracy. The present invention can be used for mathematical expression of molecular shape, shape comparison of drug molecules, and pharmacophore comparison of drug molecules, which comparisons, in turn, useful for virtual screening of drug molecules.

DETAILED DESCRIPTION OF PREFERRED EMBODIMENTS

Figure 1:
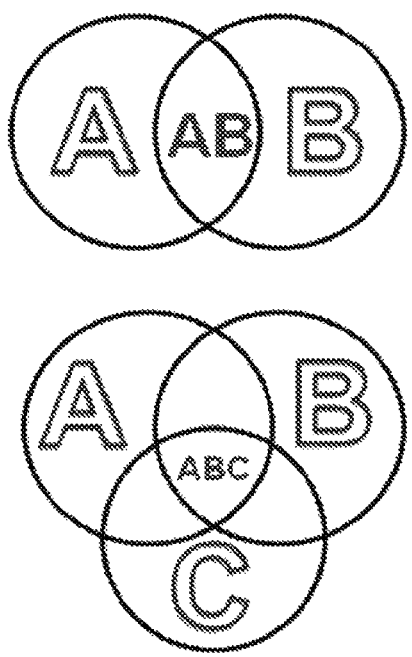
FIG. 1 is a schematic view showing the calculation of molecular overlap volume.

The present invention will now be described in more detail with reference to preferred examples in combination with the drawings.

The present invention proposed a quantitative comparison method for molecular three-dimensional shape, with reduced complexity of calculation for quantitative comparison of three-dimensional shapes of molecules and increased calculation accuracy.

In formulas (1) and (2), Gaussian function $g_i(r)$ is used instead of hard sphere density function $f_i(r)$, while the remaining part of the formulas (1) and (2) keeps unchanged. The Gaussian volume density for each of the atoms in an molecule is expressed in Formula (3):

$$g_i(r) = pe^{-\left(\frac{3p\pi^{1/2}}{4\sigma_i^3}\right)^{2/3}(r-r_i)^2}, \qquad (3)$$

wherein r represents coordinate of any point, $r_i$ represents the coordinate of atom i, $\sigma_i$ represents the van der Waals radius of the atom, and p is an adjustable factor typically with a value of 2.7. Due to the simplicity of summation and derivation of Gaussian function, the calculation complexity is reduced. However, when Formula (2) is used for calculating molecule shape, the number of summation of higher orders will be explosively increased, which brings challenges to the design of the algorithm. Therefore, an approximation is performed to Formula (1), i.e., molecular volume density is simplified as a simple add-up of atom volume densities:

$$G(r) = \sum_i g_i(r), \qquad \text{Formula (4).}$$

Although this approximation simplifies the calculation, the calculation accuracy is reduced because volume overlaps between atoms are completely ignored.

The self-overlap volume of a molecule obtained by Formula (4) is higher than actual molecule volume by an overestimation ratio of between 2 and 6.

Because the calculation of molecular shape similarity involves the overlap volume between molecules and the self-overlap volume of the molecule, $$S_{12} = \frac{V_{12}}{V_1 + V_2 - V_{12}}, \qquad \text{Formula (5)}$$

large error will be generated when Formula (4) is used for similarity calculation. Formula (4) is further modified to achieve a quantitative comparison method for molecular three-dimensional shape.

For any molecule consisted of N atoms, the shape of the molecule can be expressed by a volume density function, $$G(r) = \sum_{i=1}^{N} w_i p e^{-\left(\frac{3p\pi^{1/2}}{4\sigma_i^3}\right)^{2/3}(r-r_i)^2}, \qquad \text{Formula (6)}$$

wherein $w_i$ is a weight factor for atom i, $r_i$ represents the coordinate of atom i, $\sigma_i$ represents the van der Waals radius of the atom, and p is an adjustable factor which is set to a value of $2\sqrt{2}$. Such a p value enables the overlap volume for an atom Gaussian sphere with itself to equal to the volume of the atom itself, i.e, $4\pi\sigma_i^3/3$.

The determination of the weight factor is critical to the present invention. The factor eliminates, to the maximum extent, the errors caused by the simple add-up and the approximation. Because the error is originated from the double calculation of the volume of overlapping between atoms, the self-overlap volume of the molecule thus obtained is multiple times than actual value. The weight factor is an empirical function in relation to the environment of an atom in the molecule. The empirical function satisfies the following requirements:

If the atom is remote from other atoms in the molecule (for example, inert gas molecule contains only one atom), the weight factor should equal to 1; if the atom is overlapped with other atom, the factor should be less than 1 and the more the overlap, the smaller the factor.

The present invention proposes a method for determining the value of the weight factor:

$$w_i = \frac{v_i}{v_i + k\sum_{j\neq i} v_{ij}}, \quad \text{Formula (7)}$$

wherein k is a universal constant obtainable by fitting, ranged between 0.5 and 1.0. Accordingly, the overlap volume between two molecules is calculated by Formula (8):

$$V_{12} = \sum_{i \in A, j \in B} w_i w'_j v''_{ij}, \quad (8)$$

wherein, $w_i$ is the weight factor of the $i^{th}$ atom in the first molecule, $w'_j$ is the weight factor of the $j^{th}$ atom in the second molecule, $v''_{ij}$ is the overlap volume between the $i^{th}$ atom in the first molecule and the $j^{th}$ atom in the second molecule, A is the set of all the atoms in the first molecule, and B is the set of all the atoms in the second molecule.

If the first and second molecules have same 3-D structures, $V_{12}$ becomes self-overlap volume of the molecule, which is supposed to be equal to the self-volume of the molecule. The constant k is obtained by fitting the self-overlap volumes to the hard-sphere volumes for a set of diverse molecules.

Figure 2A:
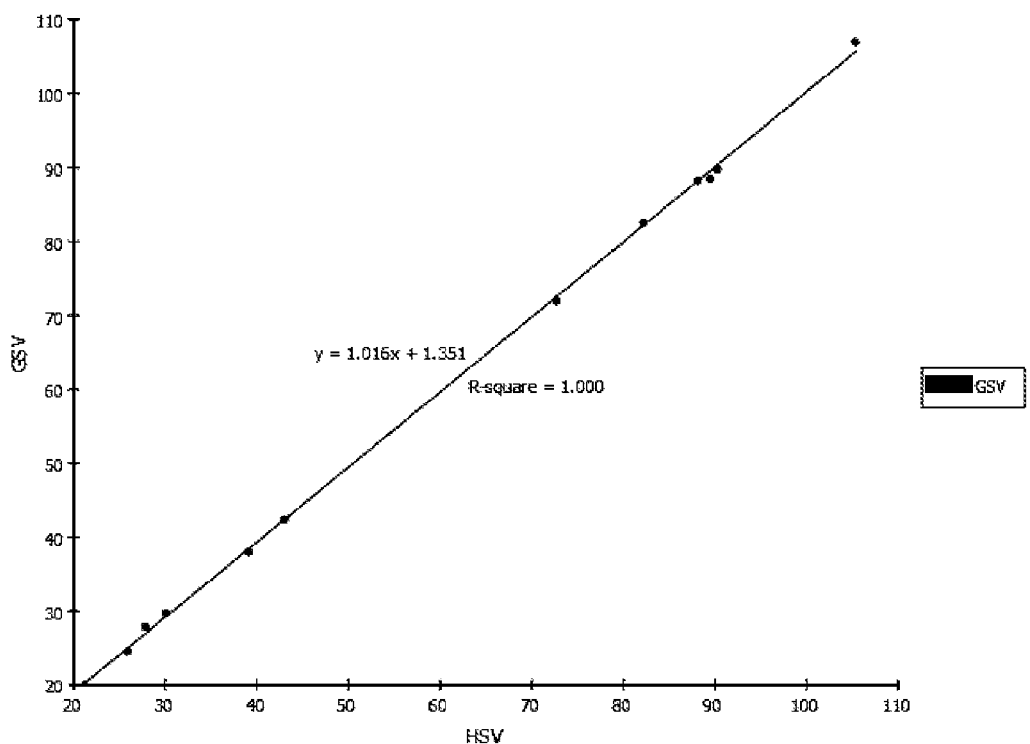
FIG. 2A shows the comparison between the molecule volumes obtained by the present method (GSV) and hard sphere model (HSV).
Figure 2B:
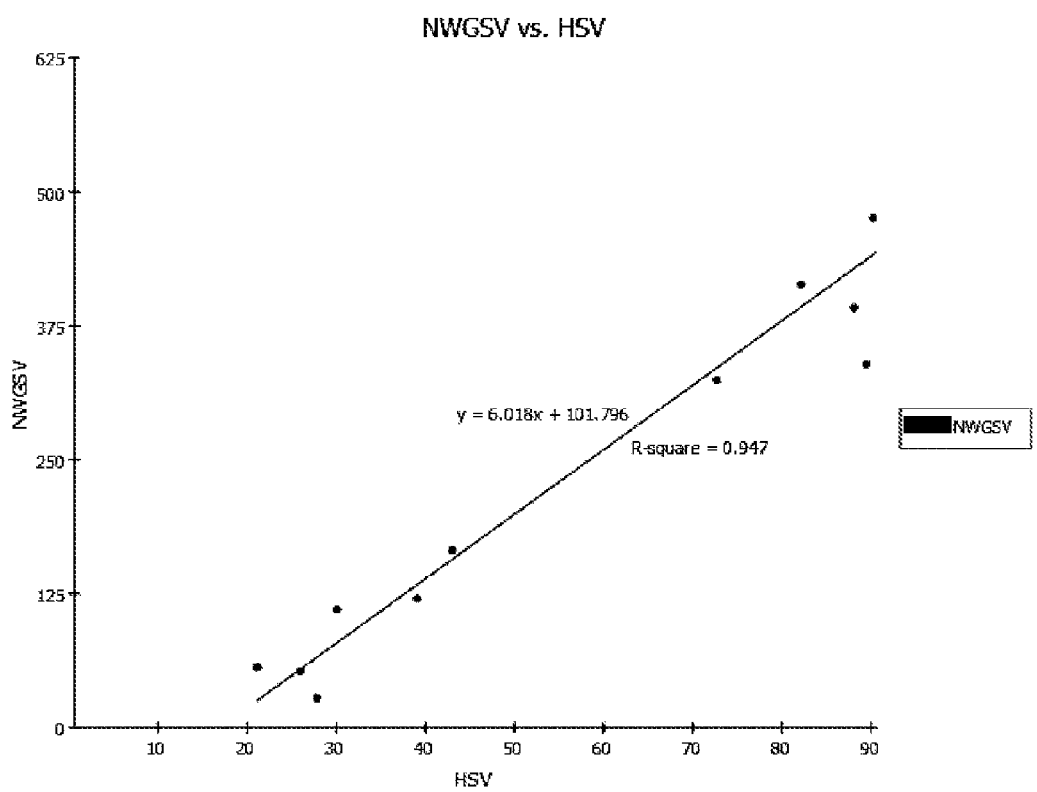
FIG. 2B shows the comparison between the molecule volumes obtained by simple add-up method and hard sphere model (HSV).

FIG. 2A shows the comparison between self-overlap volume obtained by Formula (8) and actual volume of the molecule with a correlation approaching to 1. FIG. 2B shows the relationship between self-overlap volume obtained by simple add-up method in literatures and actual volume of the molecule, indicating that the self-overlap volume computed by Formula (4) is far higher than the molecule volume, and the correlation there between is far lower than that of the present invention as shown in FIG. 2A.

Because the accuracy of the overlap volume between molecules is improved by the present invention, the accuracy of shape similarity computation of the molecules by Formula (5) is also improved.

Furthermore, the weight factor, as an empirical constant, can also be determined by the topological properties of an atom in a molecule, such as atom heterozygosity, bonding type and number, neighboring atom type, and so on. The weight factor thus determined has nothing to do with molecular configuration, which reducing the flexible overlap between molecules and also the complexity of flexible comparison of molecular shape similarity.

Example I. Calculation of Molecule Volume

Figure 3:
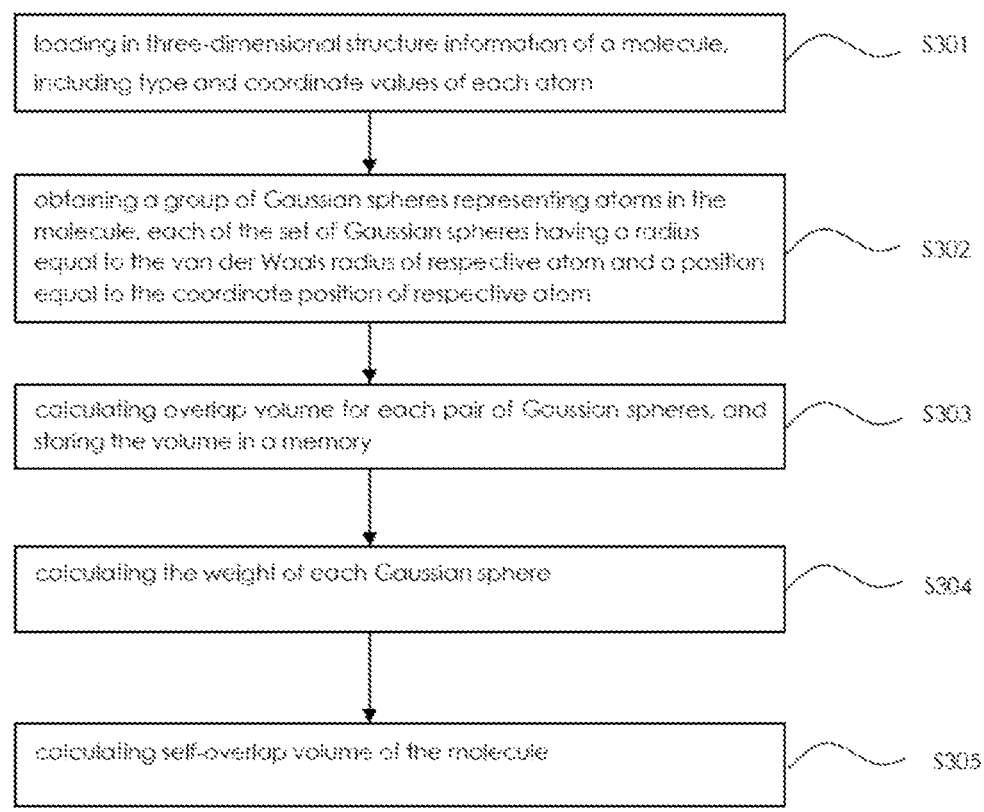
FIG. 3 is a flow chart for calculating molecule volume according to the present invention.

As shown in FIG. 3, the calculation is performed by steps of step S301, loading in three-dimensional structure information of a first molecule, the three-dimensional structure information comprising type and coordinate values of each atom contained in the first molecule;

step S302, obtaining respective van der Waals radius based on the type of respective atom contained in the first molecule, converting the three-dimensional structure information into a group of Gaussian spheres representing atoms in the first molecule, each of the set of Gaussian spheres having a radius equal to the van der Waals radius of respective atom and a position equal to the coordinate position of respective atom, the expression of Gaussian function is shown in Formula (3);

step S303, calculating overlap volume for each pair of Gaussian spheres, wherein the $ij^{th}$ pair of Gaussian spheres consists of the $i^{th}$ and the $j^{th}$ Gaussian spheres and has a overlap volume $v_{ij}$, because the product of Gaussian functions is still a Gaussian function, the overlap integral can thus simply obtained, and the overlap integral is preserved in a two-dimensional array for repeat use in subsequence calculation;

step S304, calculating the weight of each Gaussian sphere and preserving it in a one-dimensional array for later use, the weight of the $i^{th}$ Gaussian sphere being $$w_i = \frac{v_i}{v_i + k\sum_{j\neq 1} v_{ij}},$$

wherein $v_i$ is the volume of the $i^{th}$ Gaussian sphere, and k is a constant;

step S305, calculating self-overlap volume of the first molecule $$V = \sum_{i \in A, j \in A} w_i w_j v_{ij},$$

the self-overlap volume being used as a volume of the first molecule, wherein $w_i$ is the weight of the $i^{th}$ Gaussian sphere, $w_j$ is the weight of the $j^{th}$ Gaussian sphere, $v_{ij}$ is the overlap volume of the $i^{th}$ and the $j^{th}$ Gaussian spheres, and A is a set of all Gaussian sphere in the first molecule.

Figure 4:
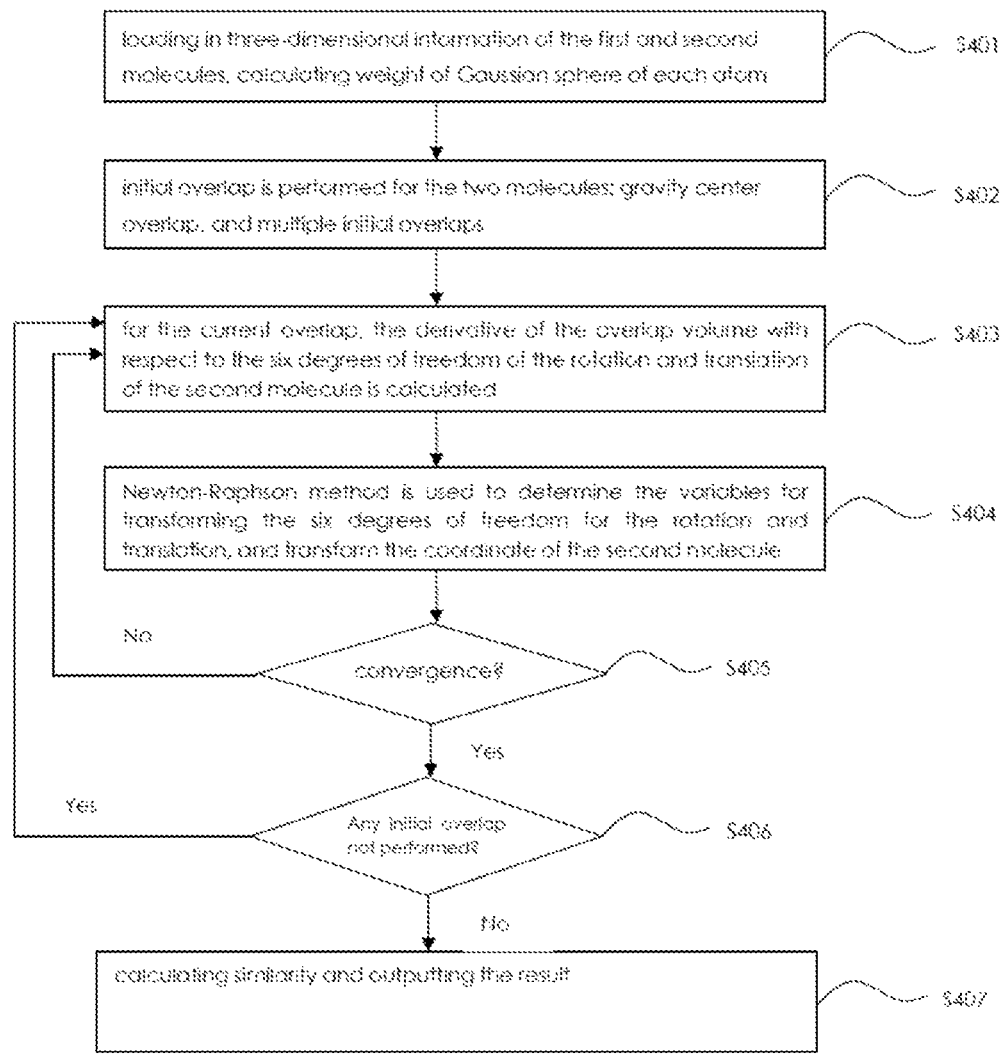
FIG. 4 is a flowchart for calculating the maximum molecule overlap and for comparing shape similarity according to the present invention.

Example II. Calculation of Maximum Overlap Volume and Shape Similarity Between Two Molecules The present example involves the maximum optimization of overlap volume between molecules, the process of which is shown in FIG. 4.

Step S401, read in the first and second molecules, the self-overlap volume of each of the molecules being calculated by way of Example I, and also the weight factor of each atom, both being preserved in the memory of a computer, specifically including loading in three-dimensional structure information of a first molecule, the three-dimensional structure information comprising type and coordinate values of each atom contained in the first molecule;

obtaining respective van der Waals radius based on the type of respective atom contained in the first molecule, converting the three-dimensional structure information into a group of Gaussian spheres representing atoms in the first molecule, each of the set of Gaussian spheres having a radius equal to the van der Waals radius of respective atom and a position equal to the coordinate position of respective atom;

calculating overlap volume for each pair of Gaussian spheres in the first molecule, wherein the $i^{th}$ pair of Gaussian spheres consists of the $i^{th}$ and the $i^{th}$ Gaussian spheres in the first molecule and has a overlap volume $v_{ij}$;

calculating the weight of each Gaussian sphere in the first molecule, the weight of the $i^{th}$ Gaussian sphere in the first molecule being $$w_i = \frac{v_i}{v_i + k\sum_{j \neq i} v_{ij}},$$

wherein $v_i$ is the volume of the $i^{th}$ Gaussian sphere in the first molecule, and k is a constant;

calculating self-overlap volume of the first molecule $$V_1 = \sum_{i \in A, j \in A} w_i w_j v_{ij},$$

wherein A is a set of all Gaussian sphere in the first molecule;

loading in three-dimensional structure information of a second molecule, the three-dimensional structure information comprising type and coordinate values of each atom contained in the second molecule;

obtaining respective van der Waals radius based on the type of respective atom contained in the second molecule, converting the three-dimensional structure information into a group of Gaussian spheres representing atoms in the second molecule, each of the set of Gaussian spheres having a radius equal to the van der Waals radius of respective atom and a position equal to the coordinate position of respective atom;

calculating overlap volume for each pair of Gaussian spheres in the second molecule, wherein the $ij^{th}$ pair of Gaussian spheres consists of the $i^{th}$ and the $i^{th}$ Gaussian spheres in the second molecule and has a overlap volume $v_{ij}'$;

calculating the weight of each Gaussian sphere in the second molecule, the weight of the $i^{th}$ Gaussian sphere in the first molecule being $$w_i' = \frac{v_i'}{v_i' + k'\sum_{j \neq i} v_{ij}'},$$

wherein $v_i'$ is the volume of the $i^{th}$ Gaussian sphere in the second molecule, and k' is a constant;

calculating self-overlap volume of the second molecule $$V_2 = \sum_{i \in B, j \in B} w_i' w_j' v_{ij}'',$$

wherein B is a set of all Gaussian sphere in the second molecule.

Step 402, initial overlap is performed for the two molecules. As a start for the maximum volume overlap, the centers of gravity of the two molecules are overlapped. The initial overlap needs not to be very accurate as a maximum optimization will be performed for the overlap volume. A simple gravity center overlap is to translate the average position, serving as the center of gravity, of each atom in each of the molecules to enable them to overlap;

During overlap optimization, one of the molecules (such as the first molecule) is fixed, and the other molecule is subject to transformation of rigid body rotation and translation, in order to obtain the maximum overlap volume through Formula (8). The transformation relates to six degrees of freedom. In this example, the Newton-Raphson method is adopted to optimize the six degrees of freedom, then perform Step S403.

Step S403, for the current overlap, the overlap volume $$V_{12} = \sum_{i \in A, j \in B} w_i w_j' v_{ij}''$$

between the first and second molecules is calculated, wherein $v^{ij''}$ is the overlap volume between the $i^{th}$ atom in the first molecule and the $j^{th}$ atom in the second molecule. The first and second derivatives of $V_{12}$, with respect to the coordinates of each atom in the second molecule is calculated, and then the derivatives are transformed onto the variables for rigid rotation and translation, to obtain the first and second derivatives of $V_{12}$, with respect to the six degrees of freedom of the rotation and translation of the second molecule.

Step S404, the Newton-Raphson method is adopted to determine the variables for transforming the six degrees of freedom for the rotation and translation of the second molecule, and transform the coordinate of the second molecule accordingly, and then perform Step S405;

Step S405, determine whether a convergence exits. If yes, perform Step S406. If no, return to Step S403.

One typical issue in optimization is multiple maxima. The purpose of this example is to obtain an overall maximum overlap volume. The solution for achieving this purpose is to adopt multiple initial overlaps (initial orientations) and select the maximum value from the optimized results. Normally, the multiple different initial overlaps can be achieved by rotation of any one of the overlaps along different axes.

Step S406, preserve the overlap volume of current initial overlap. If there is any initial overlap that is not performed, select one of the unperformed initial overlaps as current initial overlap and perform Step S403. Otherwise, select the maximum value from the overlap volumes obtained for all of the initial overlaps $V_{12}^{Max}$ as the maximum overlap volume, and perform step S407.

Step S407, calculate the similarity $$S_{12} = \frac{V_{12}^{Max}}{V_1 + V_2 - V_{12}^{Max}}$$

between the first and second molecules and output the similarity $S_{12}$ as the comparison result of the shapes of the two molecules.

The condition of convergence of step S405 is normally that the module of first-order derivative is less than a predetermined threshold.

Figure 5:
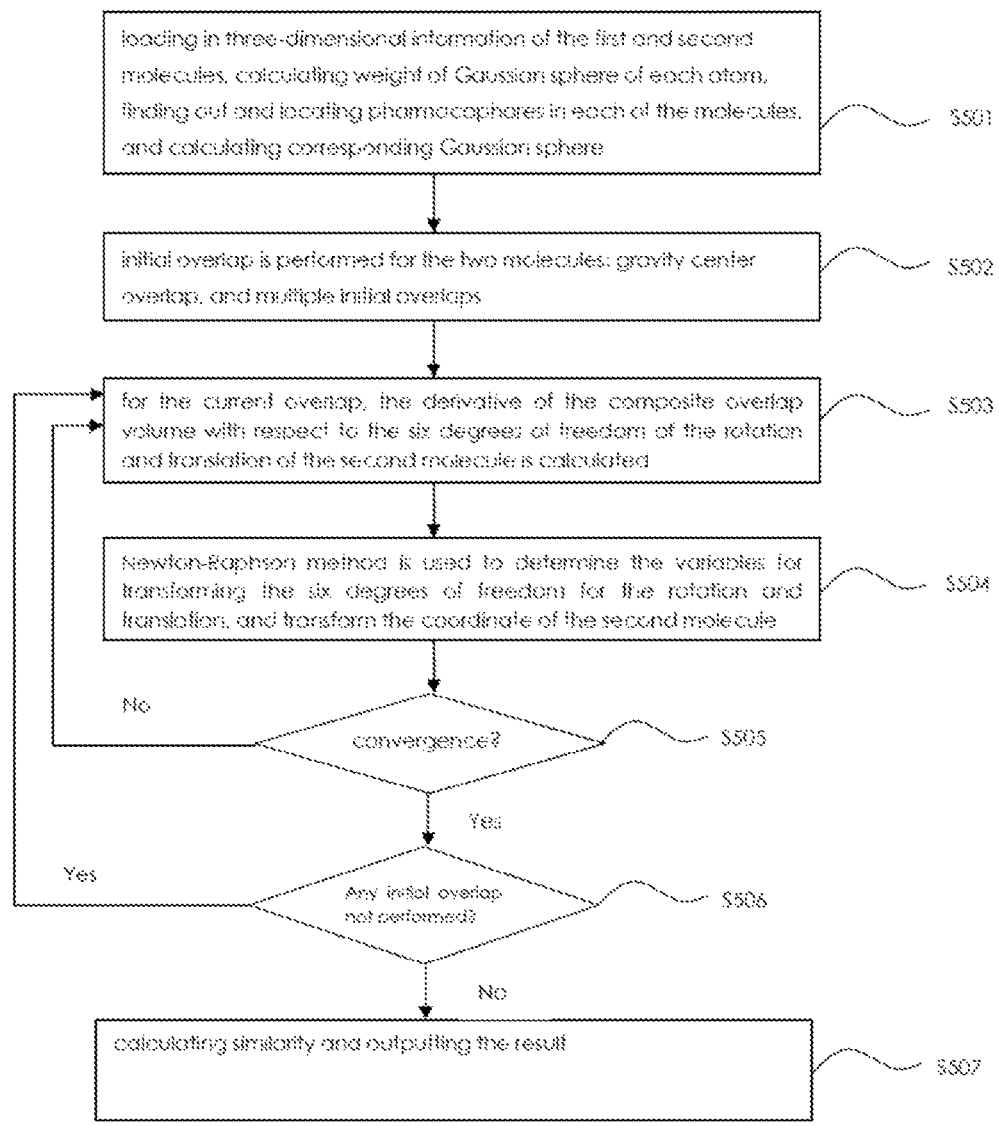
FIG. 5 is a flow chart for comparing shapes of two molecules and composite similarity of pharmacophores according to the present invention.

Example III. Comparison of Composite Similarity of Shapes and Pharmacophores Between Two Molecules The present example further incorporates the contribution of pharmacophores to the similarity comparison of molecules, which is illustrated in FIG. 5.

Step S501, read in the 3-D structural information of the first and second molecules, calculate self-overlap volume of each molecule and weight factor of each atom, find out and locate pharmacophores in each of the molecules, and store these results in the memory of a computer. Each of the pharmacophores is indicated with a Gaussian sphere with a radius of 2 angstroms. The Gaussian spheres are differently colored according to the types of the pharmacophores. For example, hydrogen bond donor is colored green, hydrogen bond receptor is colored pink, hydrophobic group is colored pearl blue, positive charge is colored red, negative charge is colored navy-blue, and so on.

To obtain the composite similarity, the overlap between the two molecules needs to be optimized. Unlike Example II, in addition to the overlap volume between the two molecules, the target functions to be optimized further include the overlap contribution between same type pharmacophores in the two molecules. Because same type pharmacophores are normally dispersed in a molecule, no weight calibration is necessary. The target function to be optimized is:

$$O_{12} = V_{12} + \sum_{i \in A, j \in B} F''_{ij}, \quad \text{Formula (9)}$$

wherein $V_{12}$, is the overlap volume between molecules obtained by Formula (8), $F_{ij}'$ is the overlap volume between the $i^{th}$ pharmacophore in the first molecule and the $j^{th}$ pharmacophore in the second molecule, and the summation over $F_{ij}'$ is limited only to the same type (color) of pharmacophores.

The self composite overlap volume $$O_1 = V_1 + \sum_{i \in A, j \in A} F_{ij}$$

of the first molecule is calculated by Formula (9), wherein $F_{ij}$ is the overlap volume between the $i^{th}$ pharmacophore and the $j^{th}$ pharmacophore in the first molecule, and the summation over $F^{ij}$ is limited only to the same type (color) of pharmacophores. The self composite overlap volume $$O_2 = V_2 + \sum_{i \in B, j \in B} F'_{ij}$$

of the second molecule is calculated by Formula (9), wherein $F_{ij}'$ is the overlap volume between the $i^{th}$ pharmacophore and the $j^{th}$ pharmacophore in the second molecule, and the summation over $F_{ij}'$ is limited only to the same type (color) of pharmacophores Step S502, initial overlap is performed for the two molecules. As a start for the maximum volume overlap, the centers of gravity of the two molecules are overlapped. The average position of each atom in each molecule, serving as the center of gravity, is translated to enable them to overlap;

During overlap optimization, one of the molecules (such as the first molecule) is fixed, and the other molecule is subject to transformation of rigid body rotation and translation, in order to obtain the maximum overlap volume through Formula (9). The transformation relates to six degrees of freedom. In this example, the Newton-Raphson method is adopted to optimize the six degrees of freedom, then perform Step S503.

Step S503, for the current overlap, the composite overlap volume $$O_{12} = V_{12} + \sum_{i \in A, j \in B} F''_{ij}$$

between the first and second molecules is calculated. The first and second derivatives of $O_{12}$ with respect to the coordinates of each atom in the second molecule is calculated, and then the derivatives are transformed onto the variables for rigid rotation and translation, to obtain the first and second derivatives of $O_{12}$ with respect to the six degrees of freedom of the rotation and translation of the second molecule.

Step S504, the Newton-Raphson method is adopted to determine the variables for transforming the six degrees of freedom for the rotation and translation of the second molecule, and transform the coordinate of the second molecule accordingly, and then perform Step S505;

Step S505, determine whether a convergence exits. If yes, perform Step S506. If no, return to Step S503.

One typical issue in optimization is multiple maxima. The purpose of this example is to obtain an overall maximum overlap volume. The solution for achieving this purpose is to adopt multiple initial overlaps (initial orientations) and select the maximum value from the optimized results. Normally, the multiple different initial overlaps can be achieved by rotation of any one of the overlaps along different axes.

Step S506, preserve the overlap volume of current composite initial overlap. If there is any initial overlap that is not performed, select one of the unperformed initial overlaps as current initial overlap and perform Step S503. Otherwise, select the maximum value from the composite overlap volumes obtained for all of the initial overlaps $O_{12}^{Max}$ as the maximum overlap volume, and perform step S507.

Step S507, calculate the similarity $$S_{12} = \frac{O_{12}^{Max}}{O_1 + O_2 - O_{12}}$$

(Formula 10) between the first and second molecules and output the similarity $S_{12}$ as the comparison result of the shapes of the two molecules.

The condition of convergence of step S505 is normally that the module of first-order derivative is less than a predetermined threshold.

Example IV. Overlap of a Set of Molecules

Figure 6:
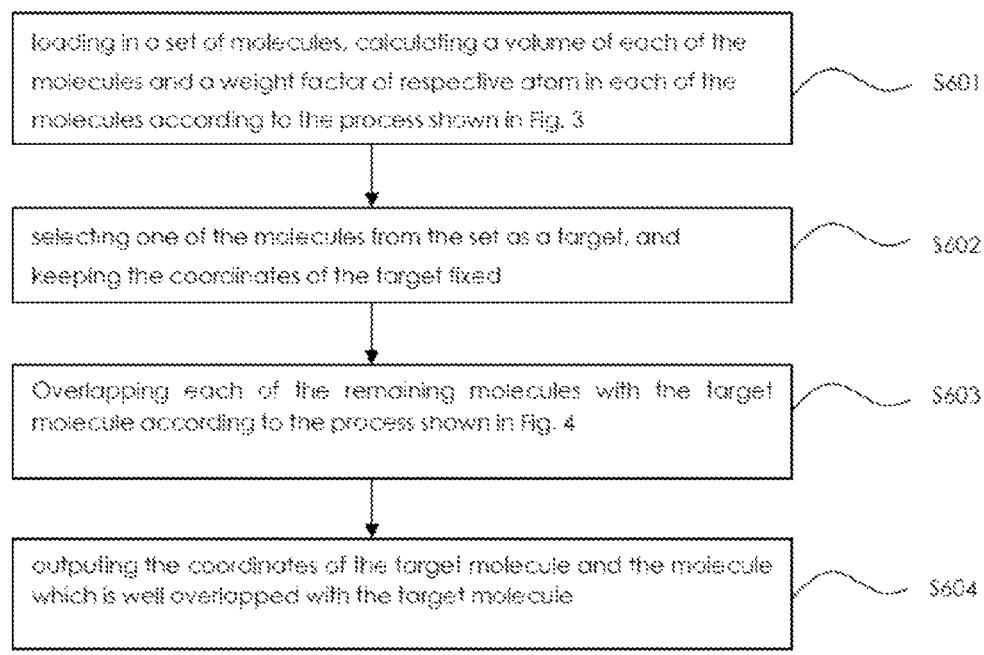
FIG. 6 is a flow chart showing the process for overlapping molecules.

The present example is an extension to Example II, which is illustrated in FIG. 6.

Step S601, a system loads in a set of molecules, calculates a volume of each of the molecules and a weight factor of respective atom in each of the molecules. The results are stored in a memory of a computer.

Step S602, select one from the set of molecules as a target. The target molecule may be the first molecule, the molecule having the largest volume, or be designated as desired. After selection, the target molecule is fixed.

Step S603, rotate and translate the remaining molecules by the method described in Example II to obtain the maximum overlap with the target molecule. Due to the multiple maxima issue, multiple initial overlap position can be adopted for each overlapping molecule, and then a optimal overlap result is selected.

Step S604, output the coordinates of the target molecule and the molecule which is well overlapped with the target molecule. The pair of overlap molecules thus obtained can be used for 3-D quantitative structure-activity relationship (QSAR) analysis or the establishment of pharmacophore model.

The invention claimed is:

1. A method for shape comparison between drug molecules, comprising steps of:
   (31) loading in three-dimensional structure information for a first molecule and a second molecule and calculating self-overlap volumes of the first and second molecules, the calculation comprising steps of:
   loading in three-dimensional structure information of the first molecule, the three-dimensional structure information comprising type and coordinate values of each atom contained in the first molecule;
   obtaining respective van der Waals radius based on the type of respective atom contained in the first molecule, converting the three-dimensional structure information into a group of Gaussian spheres representing atoms in the first molecule, each of the set of Gaussian spheres having a radius equal to the van der Waals radius of respective atom and a position equal to the coordinate position of respective atom;
   calculating overlap volume for each pair of Gaussian spheres in the first molecule, wherein the $ij^{th}$ pair of Gaussian spheres in the first molecule consists of the $i^{th}$ and the $j^{th}$ Gaussian spheres and has a overlap volume $v_{ij}$;
   calculating the weight of each Gaussian sphere in the first molecule, the weight of the $i^{th}$ Gaussian sphere in the first molecule $$w_i = \frac{v_i}{v_i + k \sum_{j \neq 1} v_{ij}},$$

wherein $v_i$ is the volume of the $i^{th}$ Gaussian sphere, and k is a constant;
   calculating self-overlap volume of the first molecule $$V_1 = \sum_{i \in A, j \in A} w_i w_j v_{ij},$$

wherein A is a set of all Gaussian sphere in the first molecule;
   loading in three-dimensional structure information of the second molecule, the three-dimensional structure information comprising type and coordinate values of each atom contained in the second molecule;
   obtaining respective van der Waals radius based on the type of respective atom contained in the second molecule, converting the three-dimensional structure information into a group of Gaussian spheres representing atoms in the second molecule, each of the set of Gaussian spheres having a radius equal to the van der Waals radius of respective atom and a position equal to the coordinate position of respective atom;
   calculating overlap volume for each pair of Gaussian spheres in the second molecule, wherein the $ij^{th}$ pair of Gaussian spheres in the second molecule consists of the $i^{th}$ and the $j^{th}$ Gaussian spheres and has a overlap volume $v_{ij}'$;
   calculating the weight of each Gaussian sphere in the second molecule, the weight of the $i^{th}$ Gaussian sphere in the second molecule $$w_i' = \frac{v_i'}{v_i' + k' \sum_{j \neq 1} v_{ij}'},$$

wherein $v_{i'}$ is the volume of the $i^{th}$ Gaussian sphere, and k' is a constant;
   calculating self-overlap volume of the second molecule $$V_2 = \sum_{i \in B, j \in B} w_i' w_j' v_{ij}',$$

wherein B is a set of all Gaussian sphere in the second molecule;
   (32) calculating intermolecular volumes of the first and second molecules in various overlap situations, selecting the maximum intermolecular volume;
   (33) determining the similarity between the first and second molecules based on the volume of the first molecule, the volume of the second molecule and the maximum intermolecular volume, the similarity being the result of the shape comparison between the two molecules; and
   determining physical and chemical properties, and bioactivity of the two molecules according to the similarity between the first and second molecules so as to perform virtual screening of the drug molecules;
   wherein the intermolecular volume of step (32) is a composite overlap volume between molecules, which is calculated by steps of:
   finding out pharmacophores and their positions in each of the molecules;
   determining types of each of the pharmacophores in each of the molecules;
   calculating a self composite overlap volume $$O_1 = V_1 + \sum_{i \in A, j \in A} F_{ij}$$

of the first molecule, wherein $F_{ij}$ is the overlap volume between the $i^{th}$ pharmacophore and the $j^{th}$ pharmacophore, and the summation over $F_{ij}$ is limited only to pharmacophores of same type;
   calculating a self composite overlap volume $$O_2 = V_2 + \sum_{i \in B, j \in B} F_{ij}'$$

of the second molecule, wherein $F_{ij}'$ is the overlap volume between the $i^{th}$ pharmacophore and the $j^{th}$ pharmacophore, and the summation over $F_{ij}'$ is limited only to pharmacophores of same type;
   calculating a composite overlap volume between the first and the second molecules $$O_{12} = V_{12} + \sum_{i \in A, j \in B} F_{ij}'',$$

wherein $F_{ij}''$ is the overlap volume between the $i^{th}$ pharmacophore in the first molecule and the $j^{th}$ pharmacophore in the second molecule, and the summation over $F_{ij}''$ is limited only to pharmacophores of same type;

calculating composite overlap volumes $O_{12}$ between the first and the second molecules under various overlap situations and selecting the maximum value $O_{12}^{Max}$ as the maximum intermolecular volume;

wherein step (33) specifically includes a step of calculating the similarity $$S_{12} = \frac{O_{12}^{Max}}{O_1 + O_2 - O_{12}}$$

between the first and second molecules and outputting the similarity $S_{12}$ as the result for the shape comparison for the two molecules.

2. The method of claim 1, wherein the intermolecular volume of step (32) is also an overlap volume between molecules, which is calculated by a step of calculating overlap volumes $$V_{12} = \sum_{i \in A, j \in B} w_i w_j' v_{ij}''$$

of the first and second molecules in various overlap situations, wherein $v_{ij}''$ is an overlap volume of the $i^{th}$ and the $j^{th}$ atoms in the first molecule, the maximum value $V_{12}^{Max}$ serves as the maximum intermolecular volume; and wherein in step (33), the similarity $$S_{12} = \frac{V_{12}^{Max}}{V_1 + V_2 - V_{12}^{Max}}$$

between the first and second molecules is calculated and served as the result of the shape comparison.

3. The method of claim 1, wherein the k is ranged between 0.5 and 1.0, and k' is ranged between 0.5 and 1.0.

* * * * *